United States Patent
Niess et al.

(10) Patent No.: US 9,237,955 B2
(45) Date of Patent: Jan. 19, 2016

(54) INTERVERTEBRAL DISC ENDOPROSTHESIS

(75) Inventors: Christine Niess, Kirchheim (DE); Roman Preuss, Kirshhelm (DE); Norbert Schneider, Schorndorf (DE); Matthias Grassel, Ostfildem (DE)

(73) Assignee: CeramTec GmbH, Plochingen (DE)

( * ) Notice: Subject to any disclaimer, the term of this patent is extended or adjusted under 35 U.S.C. 154(b) by 753 days.

(21) Appl. No.: 13/001,205

(22) PCT Filed: Jul. 1, 2009

(86) PCT No.: PCT/EP2009/058238
§ 371 (c)(1),
(2), (4) Date: May 26, 2011

(87) PCT Pub. No.: WO2010/000766
PCT Pub. Date: Jan. 7, 2010

(65) Prior Publication Data
US 2011/0218630 A1    Sep. 8, 2011

(30) Foreign Application Priority Data

Jul. 3, 2008 (DE) .......................... 10 2008 040 115

(51) Int. Cl.
*A61F 2/44*    (2006.01)
*A61L 27/10*    (2006.01)
(Continued)

(52) U.S. Cl.
CPC ............... *A61F 2/4425* (2013.01); *A61L 27/10* (2013.01); *C04B 35/119* (2013.01); *C04B 35/42* (2013.01); *A61F 2002/30331* (2013.01); *A61F 2002/30487* (2013.01); *A61F 2002/30957* (2013.01); *A61F 2310/00203* (2013.01); *A61F 2310/00233* (2013.01); *A61F 2310/00239* (2013.01); *A61L 2430/38* (2013.01); *C04B 2235/3205* (2013.01);
(Continued)

(58) Field of Classification Search
CPC ............................ A61F 2/4425; A61F 2/4455
USPC ............................................ 623/17.14–17.15
See application file for complete search history.

(56) References Cited

U.S. PATENT DOCUMENTS

| | | | |
|---|---|---|---|
| 5,667,548 | A | 9/1997 | Graule et al. |
| 6,368,350 | B1 * | 4/2002 | Erickson et al. ........... 623/17.14 |

(Continued)

FOREIGN PATENT DOCUMENTS

| | | |
|---|---|---|
| DE | 198 50 366 A1 | 5/1999 |
| DE | 103 23 363 A1 | 2/2004 |

(Continued)

*Primary Examiner* — Eduardo C Robert
*Assistant Examiner* — Stuart S Bray
(74) *Attorney, Agent, or Firm* — Norton Rose Fulbright US LLP

(57) ABSTRACT

An intervertebral disc endoprosthesis for implantation in the spinal column, with an upper end plate and a lower end plate for securing respectively to the bones of the vertebral body, and with a slide bearing which is arranged between the end plates and is composed of slide bodies that are designed to slide on each other. both end plates are made of plastic and the slide bodies are made of ceramic, the slide bodies are encapsulated by the plastic of the end plates and the surface areas of the slide bodies encapsulated by the plastic of the end plates have surface area enlargements by comparison with flat surfaces. To ensure that the slide bodies are connected fixedly to the end plates in a manner secure against twisting, it is proposed that the surface area enlargements are elevations or depressions on the slide bodies.

9 Claims, 1 Drawing Sheet

(51) Int. Cl.
　　*C04B 35/119* 　　(2006.01)
　　*C04B 35/42* 　　(2006.01)
　　*A61F 2/30* 　　(2006.01)

(52) U.S. Cl.
　　CPC . *C04B 2235/3213* (2013.01); *C04B 2235/3217* (2013.01); *C04B 2235/3222* (2013.01); *C04B 2235/3224* (2013.01); *C04B 2235/3225* (2013.01); *C04B 2235/3227* (2013.01); *C04B 2235/3229* (2013.01); *C04B 2235/3241* (2013.01); *C04B 2235/3246* (2013.01); *C04B 2235/3886* (2013.01); *C04B 2235/5292* (2013.01)

(56) References Cited

U.S. PATENT DOCUMENTS

| | | | |
|---|---|---|---|
| 6,452,957 B1 | 9/2002 | Burger et al. | |
| 7,025,787 B2 * | 4/2006 | Bryan et al. | 623/17.16 |
| 7,250,060 B2 * | 7/2007 | Trieu | 623/17.15 |
| 7,255,714 B2 * | 8/2007 | Malek | 623/17.15 |
| 7,582,115 B2 * | 9/2009 | Weber | 623/17.14 |
| 7,641,692 B2 * | 1/2010 | Bryan et al. | 623/17.15 |
| 7,740,658 B2 * | 6/2010 | Eckman | 623/17.11 |
| 7,815,679 B2 * | 10/2010 | Khalili | 623/17.15 |
| 7,905,919 B2 * | 3/2011 | Kellar et al. | 623/16.11 |
| 7,909,876 B2 * | 3/2011 | Dooris et al. | 623/17.14 |
| 8,021,428 B2 * | 9/2011 | Bartish et al. | 623/17.15 |
| 8,070,823 B2 * | 12/2011 | Kellar et al. | 623/23.4 |
| 8,097,038 B2 * | 1/2012 | Malek | 623/17.16 |
| 8,192,496 B2 * | 6/2012 | Peukert et al. | 623/17.15 |
| 8,197,546 B2 * | 6/2012 | Doubler et al. | 623/17.15 |
| 8,262,731 B2 * | 9/2012 | Songer et al. | 623/17.14 |
| 8,343,222 B2 * | 1/2013 | Cope | 623/17.14 |
| 8,372,150 B2 * | 2/2013 | Humphreys et al. | 623/17.15 |
| 2003/0135278 A1 * | 7/2003 | Eckman | 623/17.14 |
| 2004/0024460 A1 * | 2/2004 | Ferree | 623/17.12 |
| 2004/0111160 A1 * | 6/2004 | Evans et al. | 623/17.14 |
| 2005/0060036 A1 * | 3/2005 | Schultz et al. | 623/17.15 |
| 2005/0080488 A1 * | 4/2005 | Schultz | 623/17.13 |
| 2005/0159818 A1 * | 7/2005 | Blain | 623/17.15 |
| 2005/0256581 A1 * | 11/2005 | Songer et al. | 623/17.16 |
| 2006/0259144 A1 * | 11/2006 | Trieu | 623/17.13 |
| 2006/0287728 A1 * | 12/2006 | Mokhtar et al. | 623/17.14 |
| 2007/0100453 A1 * | 5/2007 | Parsons et al. | 623/17.14 |
| 2007/0100454 A1 * | 5/2007 | Burgess et al. | 623/17.14 |
| 2007/0100456 A1 * | 5/2007 | Dooris et al. | 623/17.14 |
| 2007/0118223 A1 * | 5/2007 | Allard et al. | 623/17.13 |
| 2007/0135923 A1 * | 6/2007 | Peterman et al. | 623/17.14 |
| 2007/0162137 A1 * | 7/2007 | Kloss et al. | 623/17.15 |
| 2007/0168037 A1 * | 7/2007 | Posnick | 623/17.14 |
| 2007/0168038 A1 * | 7/2007 | Trieu | 623/17.15 |
| 2007/0185577 A1 * | 8/2007 | Malek | 623/17.11 |
| 2007/0191952 A1 * | 8/2007 | Bernero | 623/17.15 |
| 2007/0213821 A1 * | 9/2007 | Kwak et al. | 623/17.11 |
| 2007/0265707 A1 * | 11/2007 | Marnay et al. | 623/17.16 |
| 2008/0015698 A1 * | 1/2008 | Marino et al. | 623/17.15 |
| 2008/0051901 A1 * | 2/2008 | de Villiers et al. | 623/17.16 |
| 2008/0058940 A1 * | 3/2008 | Wu et al. | 623/17.15 |
| 2008/0109081 A1 * | 5/2008 | Bao et al. | 623/17.15 |
| 2008/0133011 A1 * | 6/2008 | de Villiers et al. | 623/17.11 |
| 2008/0133014 A1 * | 6/2008 | Gately et al. | 623/17.16 |
| 2008/0140204 A1 * | 6/2008 | Heinz | 623/17.16 |
| 2008/0154383 A1 * | 6/2008 | Lechmann et al. | 623/18.11 |
| 2009/0005872 A1 * | 1/2009 | Moumene et al. | 623/17.16 |
| 2009/0192616 A1 * | 7/2009 | Zielinski | 623/17.16 |
| 2009/0210059 A1 * | 8/2009 | McCombe et al. | 623/17.14 |

FOREIGN PATENT DOCUMENTS

| | | |
|---|---|---|
| DE | 103 23 363 A1 | 12/2004 |
| WO | WO 92/02470 A1 | 2/1992 |
| WO | WO 92/02470 A1 | 12/1992 |
| WO | WO 94/02429 | 2/1994 |
| WO | WO 94/24064 A1 | 10/1994 |
| WO | WO 2006/119068 A2 | 11/2006 |
| WO | WO 2006/119088 A | 11/2006 |

* cited by examiner

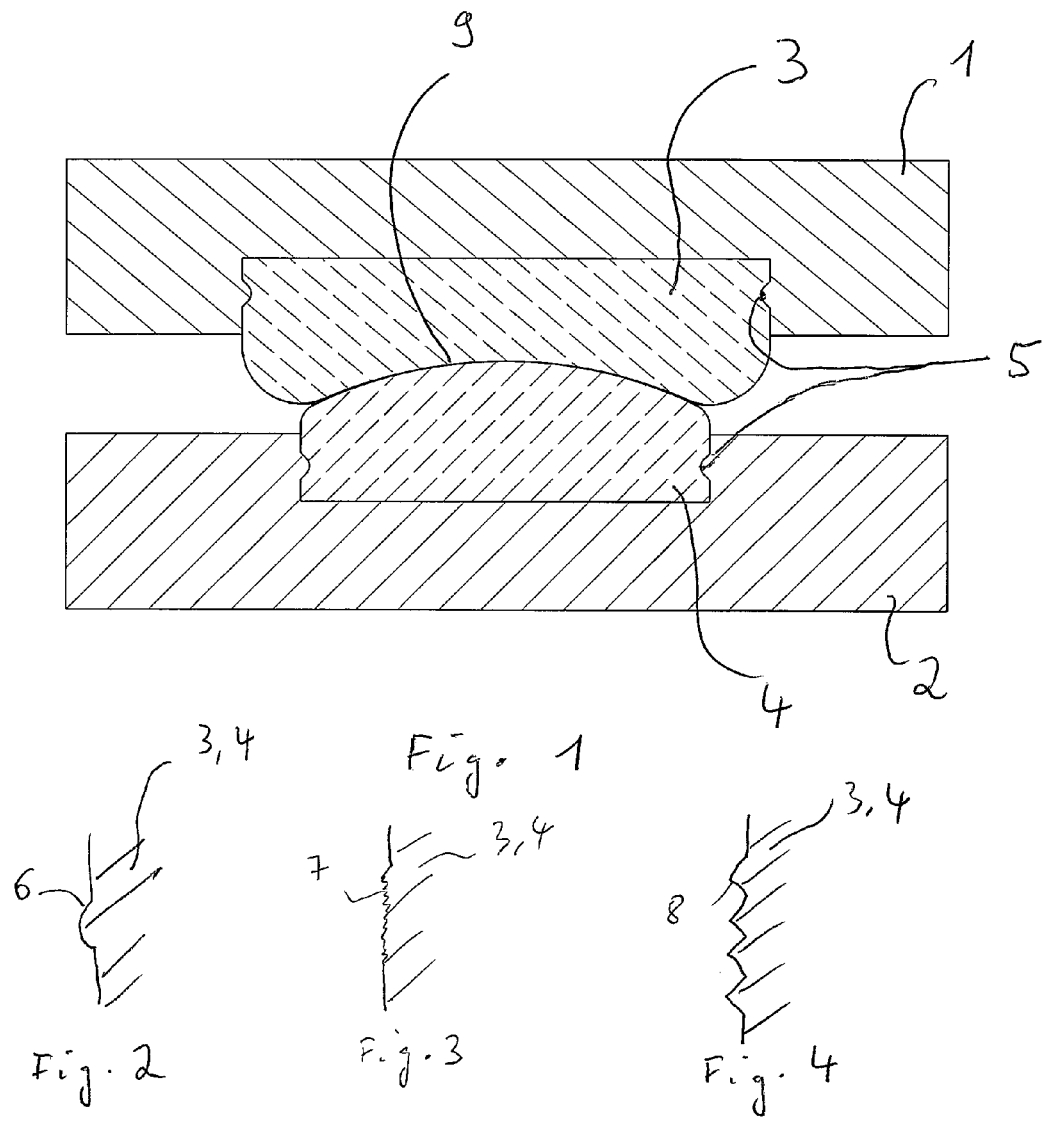

INTERVERTEBRAL DISC ENDOPROSTHESIS

RELATED APPLICATIONS

This application is a §371 of PCT/EP2009/058238 filed Jul. 1, 2009, which claims priority from DE 10 2008 040 1153 filed Jul. 3, 2008, incorporated by reference.

FIELD OF THE INVENTION

The invention relates to an intervertebral disc endoprosthesis for implantation in the spinal column.

BACKGROUND OF THE INVENTION

Intervertebral disc endoprostheses (total disc replacements) which exist at present are composed of two metal end plates which are intended to allow ingrowth of the adjacent bone of the vertebral bodies owing to their macroscopic and microscopic surface texture and any additional bioactive coatings (e.g. hydroxyapatite). Into each of these end plates are integrated, in the so-called "fixed ball and socket" principle, a hood-shaped and a cap-shaped sliding surface made of metal, plastic or ceramic which by their sliding on each other preserves or reconstructs the mobility of the segment operated on. All metal end plates have the disadvantage of more or less pronounced undesired artefacts in magnetic resonance imaging (MRI), which impairs the quality of the images produced.

US 2007/0135923 A1 discloses an intervertebral disc endoprosthesis for implantation in the spinal column, with an upper end plate and a lower end plate for securing respectively to the bones of the vertebral bodies, and with a sliding bearing which is arranged between the end plates and is composed of sliding bodies that are designed to slide on each other, both end plates being made of plastic and the sliding bodies being made of ceramic, the sliding bodies being encapsulated by the plastic of the end plates, and the surface regions of the sliding bodies encapsulated by the plastic of the end plates having surface-area enlargements by comparison with flat surfaces.

OBJECTS AND SUMMARY OF THE INVENTION

The object on which the invention is based is to improve an intervertebral disc endoprosthesis according to the present invention so that the sliding bodies are connected permanently fixedly to the end plates in a manner secure against twisting. Furthermore, the sliding bodies should have extreme hardness, so that no abrasion occurs over the entire period of service.

According to the invention, this object is achieved in that the surface-area enlargements are elevations or depressions on the sliding bodies. These may or may not be designed rotationally symmetrically with respect to the longitudinal axis of the intervertebral disc endoprosthesis. These surface-area enlargements are filled or surrounded by the plastic during injection moulding. As a result, the sliding bodies are connected permanently fixedly to the end plates in a manner secure against twisting.

BRIEF DESCRIPTION OF THE FIGURES

FIG. 1 shows an embodiment according to the invention.
FIG. 2 shows an embodiment of the invention having an elevation.
FIG. 3 shows an embodiment of the invention having a roughening.
FIG. 4 shows an embodiment of the invention having spikes.

DETAILED DESCRIPTION

In one embodiment according to the invention, the surface-area enlargements are roughenings. The depth of the roughenings must be chosen so that sufficient security against twisting is achieved.

In another embodiment according to the invention, the surface-area enlargements are clearances in the sliding bodies. The plastic of the end plates penetrates into these clearances and thereby produces a fixed connection secure against twisting.

In one embodiment according to the invention, the clearances are at least one circumferential groove on the outer circumference of the sliding bodies. Circumferential grooves are easy to produce and result in a fixed connection secure against twisting. These grooves are to be made in the sliding bodies either before or after the sintering. Preferably, they are made in the green body before the sintering.

In another embodiment according to the invention, the elevations are spikes. These spikes also produce a fixed connection secure against twisting.

Preferably, the intervertebral disc endoprosthesis according to the invention is used on a cervical spinal column or lumbar spinal column.

As a result of using plastic end plates, which are made of PEEK or PEKK for example and are preferably coated on the bone side, MRI artefacts are avoided and at the same time bone ingrowth is made possible. These plastic end plates produced by injection moulding integrate the sliding bodies made of ceramic. To prevent the sliding bodies from falling out and to ensure securing against rotation, a roughened surface (micro form-fit), clearances or geometrical elements of a different kind are necessary in the encapsulated part of the sliding partners, which are filled or surrounded by the plastic during injection moulding, for example in the form of a circumferential groove, bores or elevations, such as spikes for example.

It has furthermore been found that the achievement of the present object requires sliding bodies (also referred to as sintered shaped bodies or sintered bodies below) with a very specific composition. In addition to the transformation reinforcement that is attained as a result of the incorporation of a zirconium dioxide, which contains stabilising oxides, in a ceramic matrix, in accordance with a first embodiment the invention provides a mixed crystal of aluminium-oxide/chromium-oxide as the matrix. Furthermore, the invention provides that the zirconium dioxide, incorporated in the matrix, and the chromium oxide, forming the mixed crystal together with the aluminium oxide, are in a specific molar ratio with respect to each other. This measure makes it possible for the first time for hardness values to be attained, even with comparatively high proportions of zirconium dioxide that may be required in order to obtain particularly good fracture toughness, that have not been attainable hitherto with corresponding proportions of zirconium dioxide. On the other hand, with low proportions of zirconium dioxide there may even be a relatively small chromium-oxide content, which counteracts embrittlement of the material. According to its first embodiment, the invention therefore provides a sintered material according to claim 6 for solving the present problem.

The specification that the zirconium dioxide, containing the stabilising oxides, and chromium oxide, should be present in a specific molar ratio necessarily also results in specific relationships for the other components, since, for example, with a falling proportion of zirconium dioxide, the proportions of stabilising oxides, relative to the sintered shaped body, also decrease, whilst, on the other hand, the proportion of aluminium oxide rises. Relative to the aluminium oxide of the sintered shaped body, the chromium oxide is present in a weight quantity of 0.004 to 6.57% by weight, although it must not be disregarded that chromium oxide and the zirconium dioxide, containing the stabilising oxides, are in the specified molar ratio. Of the stabilising oxides, cerium oxide has proved to be very particularly preferable.

According to a further advantageous embodiment, the proportion of the matrix material in the sintered shaped body amounts to at least 70% by volume—and is formed of an aluminium-oxide/chromium-oxide mixed crystal with a chromium oxide proportion of 0.01 to 2.32% by weight, relative to aluminium oxide, wherein 2 to 30% by volume of zirconium dioxide is incorporated in the matrix and the zirconium dioxide contains 0.27 to 2.85 mol % of yttrium oxide, relative to the mixture of zirconium dioxide and yttrium oxide, and the zirconium dioxide is present predominantly in the tetragonal modification with an average grain size that does not exceed 2 $\xi$m. A quantity of 0.27 to 2085 mol % of yttrium oxide, relative to the mixture of zirconium dioxide and yttrium oxide, corresponds to 0.5 to 5.4% by weight of yttrium oxide, relative to zirconium dioxide. In the case of such a sintered shaped body, the molar ratio between the zirconium dioxide, containing the yttrium oxide, and chromium oxide is 370:1 to 34:1.

According to a further particularly preferred embodiment of the invention, the matrix material consists of an aluminium-oxide/chromium-oxide mixed crystal and further mixed crystal of the formula $SrAl_{12-x}Cr_xO_{19}$, wherein x has a value of 0.0007 to 0.045. In this embodiment too, which otherwise corresponds to the first embodiment, an effect that increases the toughness results from the zirconium dioxide that is incorporated in the mixed-crystal matrix, whilst the chromium addition can counteract any drop in the hardness values due to the proportion of zirconium dioxide. The mixed crystal of the formula. $SrAl_{12-x}Cr_xO_{19}$ that is additionally formed by the addition of strontium oxide now has the additional effect that, even at higher temperatures, it imparts to the sintered shaped body a further improved toughness. The wear resistance of these sintered shaped bodies under the influence of raised temperatures is therefore also improved. In this embodiment too, the cerium oxide has proved to be particularly suitable.

The term mixed crystal used in the claims and description is to be understood not in the sense of monocrystal, but rather it means a solid solution of chromium oxide in aluminium oxide or strontium alumina. The sintered shaped body, or sliding bodies, according to the invention is polycrystalline.

According to a further embodiment, the wear resistance of the sintered shaped bodies can be further improved as a result of the incorporation in the matrix material of 2 to 25% by volume of one or more carbides, nitrides or carbonitrides of the metals of the 4th and 5th subgroups of the periodic system of the elements—relative to the matrix material. The proportion of these hard materials is preferably 6 to 15% by volume. Titanium nitride, titanium carbide and titanium carbonitride are particularly suitable.

According to a particularly preferred further embodiment of the invention, the molar ratio of the zirconium dioxide, containing the stabilising oxides, to chromium oxide is adjusted as a function of the proportion of zirconium dioxide present in the sintered shaped bodies according to the invention in such a way that, with low proportions of zirconium dioxide, there are also small quantities of chromium oxide present. What has proved to be very particularly in this connection is an adjustment of the molar ratio of zirconium dioxide:chromium oxide so that it is in the range of 2-5% by volume; zirconium dioxide 1,000:1-100:1
>5-15% by volume zirconium dioxide 200:1-40:1
>15-30% by volume; zirconium dioxide 100:1-20:1
>30-40% by volume; zirconium dioxide 40:1-20:1.

In order to adjust the zirconium dioxide so that it is present predominantly in the tetragonal modification, it is necessary in accordance with the invention for a grain size of the zirconium dioxide that does not exceed 2 μm to be set. Apart from the proportions of zirconium dioxide in the cubic modification which are permitted in a quantity of up to 5% by volume, in addition small quantities of the monoclinic modification are also permitted, although these should also not exceed a maximum quantity of 5% by volume and preferably are less than 2% by volume, a quantity of even less than 1% by volume being very particularly preferred, so that preferably more than 90% by volume are present in the tetragonal modification.

Since the sintered shaped body further contains, in addition to the components specified in the claims, only impurities that have been unavoidably dragged in and which, in accordance with a further preferred embodiment of the invention, amount to no more than 0.5% by volume, the sintered shaped body merely consists of the aluminium-oxide/chromium-oxide mixed crystal or of this mixed crystal and the mixed crystal of the formula $SrAl_{12-x}Cr_xO_{19}$—and also of the zirconium dioxide that contains the stabilising oxides and is incorporated in the matrix consisting of the mixed crystals mentioned. Further phases, such as, for example, grain-boundary phases, which are formed when aluminium oxide and magnesium oxide are used together, or further crystalline phases, as develop in the case of the additions of substances known from the prior art, such as YNbO or YTaO, and which have an insufficiently high softening point, are not present in the sintered shaped body according to the invention. The oxides of Mn, Cu, Fe that are known from the prior art and which likewise result in the development of further phases, also give rise to a reduced softening point and result in low edge strength. The use of these materials is therefore precluded in the case of the invention.

The zirconium dioxide is preferably present in a quantity of not more than 30% by volume. The zirconium dioxide is preferably present also in a quantity of less than 15% by volume. If between 15 and 30% by volume of zirconium dioxide is present, the molar ratio between the zirconium dioxide, containing the stabilising oxides, and chromium oxide lies very particularly preferably between 40:1 and 25:1.

According to a further very particularly preferred embodiment, the proportion of zirconium dioxide present in tetragonal modification is more than 95% by volume, with the total proportion that is present in the cubic and/or monoclinic modification being merely up to 5% by volume. The observance of a grain size of the incorporated zirconium dioxide in the range of 0.2 to 1.5 μm is very particularly preferred. On the other hand, an average grain size of the aluminium-oxide/chromium-oxide mixed crystal in the range of 0.8 to 1.5 μm has proved to be particularly suitable. In addition, if carbides, nitrides and carbonitrides of the metals of the 4th and 5th subgroups of the periodic system of the elements are also used, these are used with a grain size of 0.8 to 3 μm. The grains of the mixed crystal of the formula $SrAl_{12}Cr_xO_{19}$ have a length/thickness ratio in the range of 5:1 to 15:1. Their maximum length in this connection amounts to 12 μm, their maximum thickness being 1.5 μm.

The Vickers hardness of the sintered shaped bodies in accordance with the invention is greater than 1,750 [$HV_{0.5}$], but preferably is more than 1,800 [$HV_{0.5}$].

The microstructure of the sintered shaped bodies in accordance with the invention is free of microcracks and has a degree of porosity of not more than 1.0%. The sintered shaped body can also contain whiskers, although not of silicon carbide.

The sintered shaped body preferably does not contain any of the substances that are widely used as grain-growth inhibitors, such as, for example, magnesium oxide.

During sintering, the stabilising oxides are dissolved in the $ZrO_2$ lattice and stabilise the latter's tetragonal modification. For the purpose of producing the sintered shaped bodies and in order to attain a structure which is free of further undesirable phases, preferably raw materials of a high purity are used, that is, aluminium oxide and zirconium dioxide with a purity of more than 99%. The degree of impurities is preferably even substantially less. In particular, $SiO_2$ proportions of more than 0.5% by volume, relative to the finished sintered shaped body, are undesirable. The unavoidable presence of hafnium oxide in a small quantity of up to 2% by weight within the zirconium dioxide is excluded from this regulation.

The production of the sintered shaped body in accordance with the invention is effected by pressureless sintering or hot-pressing of a mixture of aluminium-oxide/zirconium-dioxide/chromium-oxide and stabilising oxides, or a mixture of these components is used, to which in addition strontium oxide and/or one or more nitrides, carbides and carbonitrides of the 4th and 5th subgroups of the periodic system of the elements are added. The addition of yttrium oxide and chromium oxide can also be effected in the form of yttrium chromium oxide ($YCrO_3$), whilst the strontium oxide can preferably be added in the form of strontium salts, in particular as strontium carbonate ($SrCO_3$). The term pressureless sintering here covers both sintering under atmospheric conditions and also sintering in a protective gas or under vacuum. The shaped body is preferably first pre-sintered in a pressureless manner to 90 to 95% theoretical density and subsequently redensified by means of hot-isostatic pressing or gas-pressure sintering. The theoretical density can be increased, as a result, to a value of more than 99.5%.

Various ceramic mixtures were produced by grinding and mixing. A temporary binding agent was added to the ground mixtures and the mixtures were subsequently spray-dried. Green bodies were then pressed out from the spray-dried mixtures, and these green bodies were either sintered or pre-sintered in a pressureless manner and subjected to a gas-pressure sintering process under argon.

With the sintered body, or sliding bodies, according to the invention, the wear of the latter is almost zero. Moreover, the risk of allergy or the allergic reactions of patients and also the risk of infections is reduced.

What are the advantages of the ceramic sliding bodies according to the invention or the ceramic from which they are produced:
1. The sliding bodies of the intervertebral disc endoprosthesis have extremely low abrasion.
2. The sliding bodies are biocompatible.
3. If the sliding bodies are written on using a laser, this writing is clearly visible and legible and can thus reduce handling errors on use of the sliding bodies.
4. The sliding bodies possess extremely good tribological properties.

Further ceramics which are well-suited for the sliding bodies of the intervertebral disc endoprosthesis are described below.

Embodiment of a First Further Ceramic

Surprisingly, it has been found that platelets can be produced in the structure, not just, as described in the prior art, for example in FP-A-0 542 815, with strontium oxide, but also with other specific oxides. The precondition for the platelet formation is the development of a hexagonal crystal structure of the platelets which are to be formed in situ. If the material system $Al_2O_3$—$Cr_2O_3$—$ZrO_2$—$Y_2O_3(CeO_2)$ is used as the matrix, it is possible to provide with a great variety of oxides to form the following platelets in situ. On alloying of alkali-metal oxides, the corresponding alkali-metal $Al_{11-x}Cr_xO_{17}$ platelets are formed, on alloying of alkaline-earth metal oxides, the corresponding alkaline-earth metal $Al_{12-x}Cr_xO_{19}$ platelets are formed, on alloying of CdO, PbO, HgO, the corresponding (Cd, Pb or $HgAl_{12-x}Cr_xO_{19}$) platelets are formed, and on alloying of rare-earth metal oxides, the corresponding rare-earth metal $Al_{11-x}Cr_xCr_xO_{18}$ platelets are formed. Moreover, $La_2O_3$ can form the compound $La_{0.9}Al_{11.76-x}Cr_xO_{19}$. Platelets are also formed if the matrix contains no $Cr_2O_3$. The platelets then formed correspond to the general formulae: alkali-metal $Al_{11}O_{17}$, alkaline-earth metal $Al_{12}O_{19}$, (Cd, Pb or $HgAl_{12}O_{19}$) or rare-earth metal $Al_{12}O_{18}$.

The solution in accordance with the invention provides a sintered shaped body or an intervertebral disc endoprosthesis (both terms denote the same thing here) which as a constituent has a quite specific composition. In addition to the transformation reinforcement which is attained as a result of the incorporation of a zirconium dioxide, which contains stabilising oxides, in a ceramic matrix, the invention provides that the matrix contains a mixed crystal of aluminium-oxide/chromium-oxide. Furthermore, the invention provides that the zirconium dioxide, incorporated in the matrix, and the chromium oxide, forming the mixed crystal together with the aluminium oxide, are in a specific molar ratio with respect to each other. This measure makes it possible for particular hardness values to be attained, even with comparatively high proportions of zirconium dioxide that may be required in order to obtain particularly good fracture toughness. On the other hand, in the case of low proportions of zirconium dioxide there may even be a relatively small chromium-oxide content, which counteracts embrittlement of the material.

One or more of the oxides of cerium, praseodymium and terbium and/or yttrium oxide can be used as stabilising agent for the zirconium oxide. 10 to 15 mol % of the oxides of cerium, praseodymium and terbium and/or 0.2 to 3.5 mol of yttrium oxide, relative to the mixture of zirconium dioxide and stabilising oxides, are preferably used.

The quantity of stabilising oxides that is added is then selected so that the zirconium dioxide is present predominantly in the tetragonal modification, and the proportion of cubic modification, relative to zirconium dioxide, is 0 to 5% by volume.

The specification that the zirconium dioxide, containing the stabilising oxides, and chromium oxide, should be in a specific molar ratio results in specific relationships for the other components, since, for example, with a falling proportion of zirconium dioxide, the proportions of stabilising oxides, relative to the sintered shaped body, also decrease, whilst, on the other hand, the proportion of aluminium oxide rises. Relative to the aluminium oxide of the sintered shaped body, the chromium oxide is present in a weight quantity of 0.004 to 6.57% by weight, with the chromium oxide and the zirconium dioxide, containing the stabilising oxides, being in the specified molar ratio.

In accordance with the invention, the matrix material contains an aluminium-oxide/chromium-oxide mixed crystal and a further mixed crystal in accordance with one of the general formulae $Me^1Al_{11-x}Cr_xO_{17}$, $Me^2Al_{12-x}Cr_xO_{19}$, $Me^{2'}Al_{12-x}Cr_xO_{19}$ or $Me^3Al_{11-x}Cr_xO_{18}$, wherein $Me^1$ stands for an alkali metal, $Me^2$ stands for an alkaline-earth metal, $Me^{2'}$ stands for cadmium, lead or mercury, and $Me^3$ stands for a rare-earth metal. $La_{0.9}Al_{11.76-x}Cr_xO_{19}$ can also be added as a mixed crystal to the matrix material, in which case x can then assume values of 0.0007 to 0.045.

In accordance with the invention, as one embodiment, a sintered shaped body that has a matrix material is provided which is characterised in that
- a1) 60 to 98% by volume of the matrix material contains
- a2) 67.1 to 99.2% by volume of an aluminium-oxide/chromium-oxide mixed crystal and
- a3) 0.8 to 32.9% by volume of a further mixed crystal, which is selected from at least one mixed crystal in accordance with one of the general formulae $La_{0.9}Al_{11.76-x}Cr_xO_{19}$, $Me^1Al_{11-x}Cr_xO_{17}$, $Me^2Al_{12-x}Cr_xO_{19}$, $Me^{2'}Al_{12-x}Cr_xO_{19}$ and/or $Me^3Al_{11-x}Cr_xO_{18}$, wherein $Me^1$ stands for an alkali metal, $Me^2$ stands for an alkaline-earth metal, $Me^{2'}$ stands for cadmium, lead or mercury, and $Me^3$ stands for a rare-earth metal and x corresponds to a value or 0.0007 to 0.045, and
- b) the matrix material contains 2 to 40% by volume of stabilised zirconium dioxide.

An effect that increases the toughness results from the zirconium dioxide that is incorporated in the mixed crystal matrix, whilst the chromium addition counteracts any drop in the hardness values when the proportion of zirconium dioxide rises. The mixed crystal of the above-mentioned formulae that is additionally formed by the addition of the above-mentioned metal oxides gives rise to the effect that, even at higher temperatures, it imparts to the sintered shaped body a further improved toughness. The wear resistance of these sintered shaped bodies under the influence of raised temperatures is therefore also improved.

According to a further embodiment, the wear resistance of the sintered shaped bodies can be further improved as a result of the incorporation in the matrix material of 2 to 25% by volume of one or more carbides, nitrides or carbonitrides of the metals of the 4th and 5th subgroups of the periodic system of the elements—relative to the matrix material. The proportion of these hard materials is preferably 6 to 15% by volume. Titanium nitride, titanium carbide and titanium carbonitride are particularly suitable.

According to a particularly preferred further embodiment of the invention, the molar ratio of the zirconium dioxide, containing the stabilising oxides, to chromium oxide is adjusted as a function of the proportion of zirconium dioxide present in the sintered shaped body in such a way that, with low proportions of zirconium dioxide, there are also small quantities of chromium oxide present. What has proved to be very particularly in this connection is an adjustment of the molar ratio of zirconium dioxide:chromium oxide so that it is in the range of

| 2-5% by volume | zirconium dioxide | 1,000 | 1 to 100 |
| >5-15% by volume | zirconium dioxide | 200 | 1 to 40 |
| >15-30% by volume | zirconium dioxide | 100 | 1 to 20 |
| >30-40% by volume | zirconium dioxide | 40 | 1 to 20 |

In order to obtain the zirconium dioxide predominantly in the tetragonal modification, it is recommended in accordance with the invention for a grain size of the zirconium dioxide that does not exceed 2 μm to be set. Apart from the possible proportions of zirconium dioxide that are in the cubic modification in a quantity of up to 5% by volume, in addition small quantities of the monoclinic modification can also be present, although these should also not exceed a maximum quantity of 10% by volume and preferably are less than 5% by volume, a quantity of even less than 2% by volume being very particularly preferred.

In a preferred embodiment, the sintered shaped body in accordance with the invention further contains, in addition to the specified components, only impurities that have been unavoidably dragged in and which, in accordance with a further preferred embodiment of the invention, amount to no more than 0.5% by volume. In a particularly preferred embodiment, the sintered shaped body merely consists of the aluminium-oxide/chromium-oxide mixed crystal and one of the mixed crystals of the formulae $Me^1Al_{11-x}Cr_xO_{17}$, $Me^2Al_{12-x}Cr_xO_{19}$, $Me^{2'}Al_{12-x}Cr_xO_{19}$ or $Me^3Al_{11-x}Cr_xO_{18}$ and also of the zirconium dioxide that contains the stabilising oxides and is incorporated in the matrix consisting of the mixed crystals mentioned. Further phases, such as, for example, grain-boundary phases, which are formed when aluminium oxide and magnesium oxide are used together, or further crystalline phases, as develop in the case of the additions of substances known from the prior art, such as $YNbO_4$ or $YTaO_4$ and which have an insufficiently high softening point, are not present in this particularly preferred embodiment of the sintered shaped body in accordance with the invention. The oxides of Mn, Cu, Fe that are known from the prior art and which likewise result in the development of further phases, also give rise to a reduced softening point and result in low edge strength. The use of these materials is therefore precluded in the case of this particularly preferred embodiment.

The zirconium dioxide is preferably present in a quantity of not more than 30% by volume, but also not in a quantity of less than 15% by volume. If between 15 and 30% by volume of zirconium dioxide is present, the molar ratio between the zirconium dioxide, containing the stabilising oxides, and chromium oxide lies very particularly preferably between 40:1 and 25:1.

According to a further preferred embodiment, the proportion of zirconium dioxide present in the tetragonal modification is more than 95% by volume. The observance of a grain size of the incorporated zirconium dioxide in the range of 0.2 to 1.5 μm is very particularly preferred. On the other hand, an average grain size of the aluminium-oxide/chromium-oxide mixed crystal in the range of 0.6 to 1.5 μm has proved to be particularly suitable. In addition, if carbides, nitrides and carbonitrides of the metals of the 4th and 5th subgroups of the periodic system of the elements are also used, these are used with a grain size of 0.5 to 3 μm. The grains of the mixed crystals of the formulae $Me^1Al_{11-x}Cr_xO_{17}$, $Me^2Al_{12-x}Cr_xO_{19}$, $Me^{2'}Al_{12-x}Cr_xO_{19}$ or $Me^3Al_{11-x}Cr_xO_{18}$ have a length/thickness ratio in the range of 5:1 to 15:1. Their maximum length in this connection amounts to 12 μm, their maximum thickness being 1.5 μm.

The Vickers hardness of the sintered shaped bodies in accordance with the invention is greater than 1,750 [$HV_{0.5}$], but preferably is more than 1,800 [$HV_{0.5}$].

The microstructure of the sintered shaped bodies in accordance with the invention is free of microcracks and has a degree of porosity of not more than 1.0%. The sintered shaped body can also contain whiskers, although not of silicon carbide.

The sintered shaped body preferably does not contain any of the substances that are widely used as grain-growth inhibitors, such as, for example, magnesium oxide.

The in situ platelet reinforcement provided in accordance with the invention also occurs when the matrix contains no $Cr_2O_3$. This is provided in accordance with the invention if a drop in the hardness values does not have an adverse effect. The platelets that are formed without $Cr_2O_3$ then correspond to the general formulae $Me^1Al_{11}O_{17}$, $Me^2Al_{12}O_{19}$, $Me^{2'}Al_{12}O_{19}$ or $Me^3Al_{12}O_{18}$. Even with these sintered shaped bodies, the same preferred embodiments can in principle be made available as with the sintered shaped bodies that contain $Cr_2O_3$ in the matrix material. In this respect, the statements made above for the sintered shaped bodies with $Cr_2O_3$ in the matrix material apply in an analogous manner to the sintered shaped bodies without $Cr_2O_3$ in the matrix material.

During sintering, the stabilising oxides are dissolved in the $ZrO_2$ lattice and stabilise the latter's tetragonal modification. For the purpose of producing the sintered shaped bodies and in order to attain a structure which is free of further undesirable phases, preferably raw materials of a high purity are used, that is, aluminium oxide and zirconium dioxide with a purity of more than 99%. The degree of impurities is preferably even substantially less. In particular, $SiO_2$ proportions of more than 0.5% by volume, relative to the finished sintered shaped body, are undesirable. The unavoidable presence of hafnium oxide in a small quantity of up to 2% by weight within the zirconium dioxide is excluded from this regulation.

The production of the sintered shaped body in accordance with the invention is effected by pressureless sintering or hot-pressing of a mixture of aluminium oxide/zirconium dioxide/chromium oxide and stabilising oxides or a mixture of these components, to which in addition an alkali-metal oxide, an alkaline-earth metal oxide, CdO, PbO, HgO, a rare-earth metal oxide or $La_2O_3$ and/or one or more nitrides, carbides and carbonitrides of the 4th and 5th subgroups of the periodic system of the elements are added. Examples of mixes are specified in Table 1. The addition of yttrium oxide and chromium oxide can also be effected in the form of yttrium chromium oxide ($YCrO_3$), whilst the alkali-metal, alkali-metal earth, cadmium, lead, mercury, rare-earth metal oxides or the lanthanum oxide can preferably be added in the form of their salts, in particular as carbonates. However, the addition of ternary compounds, which are decomposed and rearranged during sintering, is also possible. Various ceramic mixtures were produced by grinding and mixing. A temporary binding agent was added to the ground mixtures and the mixtures were subsequently spray-dried. Green bodies were pressed out from the spray-dried mixtures, and these green bodies were sintered under standard conditions.

An alternative way to produce the green bodies is directly from the suspension. For this purpose, the mixture with a solids content of over 50% by volume in an aqueous suspension is ground. The pH-value of the mixture is then to be set at 4-4.5. After grinding, urea and a quantity of the enzyme urease, which is suitable for breaking down the urea, are added before this suspension is poured off into a mould. As a result of the enzyme-catalysed urea decomposition, the pH-value of the suspension is shifted to 9, whereupon the suspension coagulates. The green body thus produced is dried and sintered after removal from the mould. The sintering process can be effected in a pressureless manner, although even pre-sintering, followed by subsequent hot-iso static redensification, is possible. Further details regarding this method (DCC method) are disclosed in WO 94/02429 and in WO 94/24064, to which reference is expressly made.

The term pressureless sintering here covers both sintering under atmospheric conditions and also sintering in a protective gas or under vacuum. The shaped body is preferably first pre-sintered in a pressureless manner to 90 to 95% theoretical density and subsequently redensified by means of hot-isostatic pressing or gas-pressure sintering. The theoretical density can be increased, as a result, to a value of more than 99.5%.

A series of factors can attain substantial significance during the production of the ceramics based on the multi-component systems that have been mentioned. In particular, during the processing of the powder mixtures, the dispersion and grinding can have particular influence upon the properties of the ceramic in accordance with the invention. In this connection, the grinding method and the grinding unit itself can have an effect upon the result. Even the solids content of the grinding suspension used can also contribute to the dispersion.

The influencing parameters and their effect upon the mechanical properties are presented in greater detail in the following examples. The following combination of solids was used for the individual tests:

| | |
|---|---|
| $Al_2O_3$ | 73.11% by weight |
| $ZrO_2$ | 23.57% by weight |
| $La_2O_3$ | 2.48% by weight |
| $YCrO_3$ | 0.84% by weight |

A 60% by weight slip was used for tests T1-T4. In test T5, the solids content was reduced to 55% by weight. A vibration mill was used in order to carry out test T1. Tests T2 and T3 were carried out on a laboratory attritor mill; in T2 grinding was carried out for 1 hour, with the grinding period in T3 being 2 hours in test T4 a quantity of 30 kg was treated in a continuous attritor mill. Test T5 was carried out in the laboratory attritor for a grinding period of 2 hours.

The results of the strength analyses for the individual tests are presented in the following:

| | 4-point flexural strength | | | | |
|---|---|---|---|---|---|
| | Mean value [MPa] | Min | Max | Stand. dev. +/− | Weibull m |
| T1 | 692 | 480 | 835 | 105 | 7 |
| T2 | 789 | 297 | 942 | 162 | 4 |
| T3 | 1033 | 695 | 1243 | 113 | 10 |
| T4 | 1214 | 930 | 1373 | 93 | 15 |
| T5 | 997 | 781 | 1156 | 96 | 13 |

TABLE 1

| | Example 1 [% by weight] | Example 2 [% by weight] | Example 3 [% by weight] | Example 4 [% by weight] | Example 5 [% by weight] | Example 6 [% by weight] |
|---|---|---|---|---|---|---|
| $Al_2O_3$ | 73.30 | 58.62 | 73.60 | 84.16 | 66.95 | 63.53 |
| $Cr_2O_3$ | 0.86 | 1.20 | 0.40 | 0.10 | 0.86 | 0.78 |
| Oxide | 1.09* | 0.22** | 1.06* | 5.63*** | 0.95* | 1.06**** |

TABLE 1-continued

|  | Example 1 [% by weight] | Example 2 [% by weight] | Example 3 [% by weight] | Example 4 [% by weight] | Example 5 [% by weight] | Example 6 [% by weight] |
| --- | --- | --- | --- | --- | --- | --- |
| $ZrO_2$ | 23.47 | 38.16 | 23.14 | 8.5 | 23.64 | 29.09 |
| $Y_2O_3$ | 1.28 | 1.80 | 0.13 |  | 1.30 |  |
| $CeO_2$ |  |  | 1.67 | 1.61 |  | 5.54 |
| TiN |  |  |  |  | 6.3 |  |

*$La_2O_3$;
**$Er_2O_3$;
***$BaO$;
****$Dy_2O_3$

Embodiment of a Second Further Ceramic

According to the invention, the sliding bodies made of ceramic in another embodiment contain the following:
- 70 to 90 volume fractions of aluminium oxide with chromium doping ($Al_2O_3$:Cr),
- 12 to 22 volume fractions of zirconium oxide with Y stabilisation ($ZrO_2$:Y) and
- 1 to 5 volume fractions of strontium aluminate of the formula $SrAl_{12}$-$xCr_xO_{19}$ with variable Cr doping.

In one refinement according to the invention, the constituents zirconium oxide and strontium aluminate are incorporated in the aluminium oxide matrix.

The strontium aluminate is preferably in the form of plate-like crystallites and/or platelets.

In one inventive refinement, the material, of the cutting template is interspersed with whiskers and/or fibres or netlike structures or woven fabrics made of suitable materials.

Further features of the invention will emerge from the figures, which are described in more detail below.

FIG. 1 shows an intervertebral, disc endoprosthesis for implantation in the cervical spinal column. The intervertebral disc endoprosthesis consists of an upper end plate 1 and a lower end plate 2 made of plastic, for example PEEK or PEKK.

In each of these end plates 1, 2 is embedded a sliding body 3, 4 of a sliding bearing. This has been achieved by encapsulating the sliding bodies 3, 4 by the plastic of the end plates 1, 2. The sliding function of the sliding bearing is achieved by two surfaces 9 which slide on each other. The sliding bearing may also consist of more than two sliding bodies.

For anchoring in a manner secure against rotation, the surface regions of the sliding bodies 3, 4 encapsulated by the plastic of the end plates 1, 2 have surface-area enlargements by comparison with flat surfaces.

In FIG. 1, the surface-area enlargement is a circumferential groove 5 on the outer circumference of the sliding bodies 3, 4. The plastic of the end plates 1, 2 penetrates into this groove 5.

FIG. 2 shows in a detail an elevation 6 according to the invention on the outer circumference of the sliding bodies 3, 4.

FIG. 3 shows in a detail a roughening 7 according to the invention on the outer circumference of the sliding bodies 3, 4.

FIG. 4 shows in a detail spikes 8 according to the invention on the outer circumference of the sliding bodies 3, 4.

It is claimed:

1. An intervertebral disc endoprosthesis for implantation in the spinal column comprising:
    an upper end plate and a lower end plate for securing respectively to the bones of the vertebral bodies;
    a sliding bearing arranged between the upper end plate and the lower end plate, said sliding bearing comprising sliding bodies which slide on each other;
    wherein the upper end plate and the lower end plate are plastic;
    wherein the sliding bodies are ceramic;
    wherein the sliding bodies are encapsulated by the plastic of the upper end plate and the lower end plate;
    wherein surface regions of the sliding bodies encapsulated by the plastic of the upper and the lower end plates has a single circumferential groove therein, wherein the circumferential groove is rotationally symmetrical with respect to the longitudinal axis of the intervertebral disc endoprosthesis.

2. An intervertebral disc endoprosthesis according to claim 1, wherein the ceramic comprises zirconium dioxide having a grain size of between 0.2 and 1.5 μm.

3. An intervertebral disc endoprosthesis according to claim 2, wherein the total proportion of the zirconium dioxide that is present is in at least one of the cubic or monoclinic modifications is 0 to 5% by volume.

4. An intervertebral disc endoprosthesis according claim 2, wherein at least 90% by volume of the zirconium dioxide has the tetragonal modification.

5. An intervertebral disc endoprosthesis according to claim 1, wherein the upper end plate and the lower end plate are plastic and injection molded.

6. An intervertebral disc endoprosthesis according to claim 1, wherein the plastic comprises at least one member selected from the group consisting of PEEK or PEKK.

7. An intervertebral disc endoprosthesis according to claim 1, having a Vickers hardness greater than 1,800.

8. An intervertebral disc endoprosthesis according to claim 1, having no more than 0.5% by volume of unavoidable impurities, relative to the sintered shaped body.

9. An intervertebral disc endoprosthesis according to claim 1, wherein the ceramic comprises aluminum-oxide/chromium-oxide mixed crystal having an average grain size of 0.8 to 1.5 μm.

* * * * *